United States Patent
Balduf

(10) Patent No.: US 8,350,081 B2
(45) Date of Patent: Jan. 8, 2013

(54) PROCESS FOR PREPARATION OF METHYL METHARYLATE USING RECYCLED METHANOL

(75) Inventor: Torsten Balduf, Pfungstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 414 days.

(21) Appl. No.: 12/597,540

(22) PCT Filed: Feb. 25, 2008

(86) PCT No.: PCT/EP2008/052226
§ 371 (c)(1),
(2), (4) Date: Oct. 26, 2009

(87) PCT Pub. No.: WO2008/145418
PCT Pub. Date: Dec. 4, 2008

(65) Prior Publication Data
US 2010/0144931 A1    Jun. 10, 2010

(30) Foreign Application Priority Data
May 25, 2007   (EP) ..................... 07010475

(51) Int. Cl.
C07C 51/16    (2006.01)
C07C 67/02    (2006.01)
C08F 20/06    (2006.01)
C08F 20/10    (2006.01)

(52) U.S. Cl. .................... 562/545; 560/217; 526/317.1; 526/318

(58) Field of Classification Search .................. None
See application file for complete search history.

(56) References Cited

U.S. PATENT DOCUMENTS

| | | | |
|---|---|---|---|
| 3,979,461 A * | 9/1976 | Ancillotti et al. | 568/697 |
| 4,147,884 A | 4/1979 | Sheng et al. | |
| 4,299,999 A | 11/1981 | Mikitenko et al. | |
| 4,665,237 A * | 5/1987 | Arakawa et al. | 568/697 |
| 4,962,133 A | 10/1990 | Chromecek et al. | |
| 5,087,744 A | 2/1992 | Krabetz et al. | |
| 5,929,275 A | 7/1999 | Wada et al. | |
| 6,214,942 B1 | 4/2001 | Siol et al. | |
| 6,265,028 B1 | 7/2001 | Zhao et al. | |
| 6,657,090 B2 | 12/2003 | Rix et al. | |
| 2002/0188151 A1* | 12/2002 | Inoue et al. | 560/205 |
| 2003/0069327 A1 | 4/2003 | Walz et al. | |
| 2003/0216587 A1 | 11/2003 | Au et al. | |
| 2004/0029724 A1 | 2/2004 | Seo et al. | |
| 2006/0135833 A1* | 6/2006 | Malzkorn et al. | 585/638 |

FOREIGN PATENT DOCUMENTS

| | | |
|---|---|---|
| DE | 102 33 685 | 2/2004 |
| DE | 102 38 370 | 3/2004 |
| EP | 0 297 445 | 1/1989 |
| EP | 0 417 606 | 4/1995 |
| EP | 0 807 465 | 11/1997 |
| EP | 0 886 658 | 12/1998 |
| EP | 0 970 993 | 1/2000 |
| EP | 1 254 887 | 11/2002 |
| EP | 1 325 780 | 7/2003 |
| GB | 2 049 693 | 12/1980 |

OTHER PUBLICATIONS

U.S. Appl. No. 12/598,513, filed Nov. 2, 2009, Balduf.
U.S. Appl. No. 12/598,438, filed Nov. 2, 2009, Balduf.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to processes for production of methacrylic acid and to processes for production of methyl methacrylate.

18 Claims, 1 Drawing Sheet

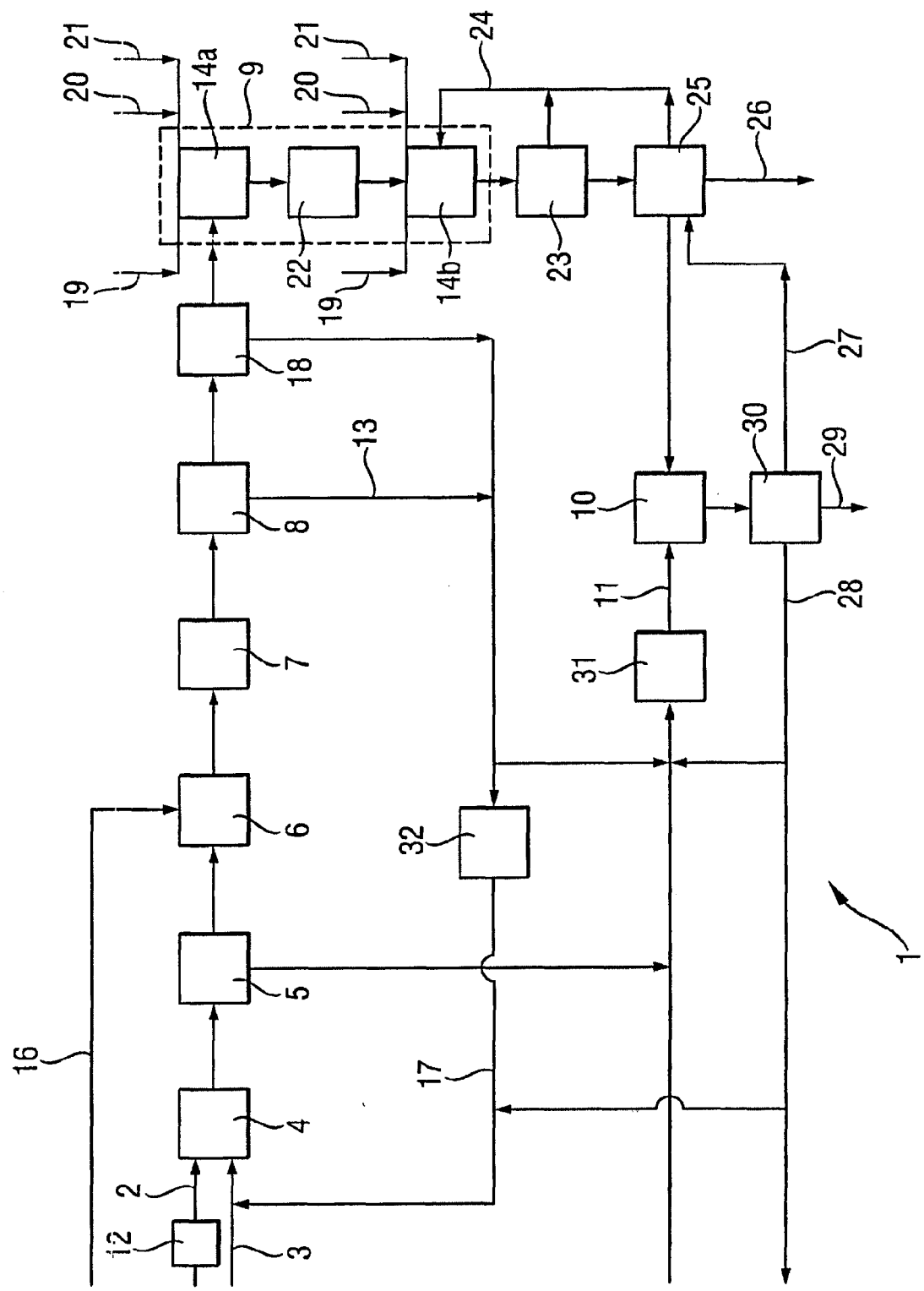

PROCESS FOR PREPARATION OF METHYL METHARYLATE USING RECYCLED METHANOL

The invention relates in general to a process for production of methacrylic acid, to a process for production of methyl methacrylate, to an apparatus for production of methacrylic acid, to an apparatus for production of methyl methacrylate, to a process carried out in the apparatus, to methacrylic acid obtainable by the process, to methyl methacrylate obtainable by the process, to methacrylate esters, to a process for preparation of a polymer comprising at least one methacrylic acid, methyl methacrylate or methacrylate ester monomer unit, to a polymer comprising at least one methacrylic acid, methyl methacrylate and/or methacrylate ester monomer unit obtainable by the process, to a process for preparation of a composition comprising at least one of methacrylic acid, methyl methacrylate, methacrylate ester, and/or a polymer, to a composition, to chemical products comprising at least one of methacrylic acid, methyl methacrylate, methacrylate ester, a polymer and/or a composition, and to the use of at least one of methacrylic acid, methyl methacrylate, methacrylate ester, a polymer and/or a composition in chemical products.

Methacrylic acid (MAA) and polymethacrylic acid (PMAA) are important industrial products with applications in, for example, thickening agents, suspending agents, flocculants, resins and absorbent materials, among other applications. A significant proportion of industrially produced MAA is, however, used in the production of its esters, in particular of methyl methacrylate and polymethyl methacrylate, as well as special esters for specific applications.

Methyl methacrylate (MMA) is itself a valuable industrial product with estimated current worldwide production of 3.3 million metric tons per year. It is principally used in the production of polymethyl methacrylate (PMMA) acrylic plastics. PMMA materials have high transparency, weathering stability and resistance to scratching, as well as being easily moulded, light and having high breaking strength. They are used, among other applications, in automobile and transportation systems, in optics and communications, in medical technology and in construction and lighting.

Other important applications are in the production of co-polymers such as the co-polymer methyl methacrylate-butadiene-styrene (MBS), which is used as a modifier for PVC; in paints and varnishes such as waterborne coatings, for example latex house paint; in adhesives; and more recently in plates that keep light spread evenly across LCD computer and TV screens, for example in flat screens, and in contact lenses. Methyl methacrylate is also used in preparation of corrosion casts of anatomical organs, such as coronary arteries of the heart.

Special methacrylate ester derivatives, for example, of alkyl and aryl alcohols, hydroxyalcohols, polyethylene glycols, quaternary ammonium derivatives and aminoalcohols, among others, have applications in, for example, contact lenses, coatings, drug delivery, controlled release of active substances, adhesives, lubricants, flow improvers, compatibility agents for polymer blends, bonding agents, food packaging, lacquers and PVC-free underseal compounds for automobile manufacture.

Various processes are known in the art for preparing methyl methacrylate, such as those based on hydrolysis of acrylonitrile or on the reaction of acetylene, carbon monoxide and an alcohol in the presence of a nickel carbonyl complex. An acetone cyanohydrin (ACH) route, with acetone and hydrogen cyanide as raw materials, is also applied. A disadvantage of these routes is the extremely high toxicity of nickel carbonyl and acetone cyanohydrin.

A preferred route is the esterification of methacrylic acid with methanol.

According to a widely used industrial process for preparation of methacrylic acid, isobutylene or tertiary butyl alcohol (TBA) is oxidised on suitable catalysts, first to methacrolein and then further to methacrylic acid. Either the methacrolein or the methacrylic acid can then be esterified with methanol, in the case of methacrolein in an oxyesterification reaction, to form methyl methacrylate.

So-called oxyesterification processes are known, for example from U.S. Pat. No. 4,060,545, U.S. Pat. No. 4,014,925, U.S. Pat. No. 3,925,463, U.S. Pat. No. 3,758,551, U.S. Pat. No. 5,670,702, U.S. Pat. No. 6,107,515 where oxidation of propylene, isobutylene, acrolein or methacrolein and esterification of the oxidised product to an acrylate or a methacrylate takes place in the same reactor.

$C_4$ fractions supplied directly from crackers do not generally comprise isobutylene in sufficiently high purity for direct use in oxidation to methacrolein and/or methacrylic acid, since they contain inter alia other unsaturated $C_4$ compounds which can also undergo oxidation to form undesired products which can only be separated with difficulty from the desired methacrolein, methacrylic acid and/or methyl methacrylate and thereby decrease the efficiency of the overall process. In addition, these other unsaturated $C_4$ compounds can poison the catalyst, necessitating more frequent regeneration and thus down-times, or result in shorter catalyst lifetimes. As such, a cracker $C_4$ effluent is thus generally not suitable for direct oxidation to methacrolein, methacrylic acid and/or methyl methacrylate and isobutylene must generally be isolated from such a $C_4$ fraction before it can be subjected to oxidation to methacrolein and/or methacrylic acid. Separation of isobutylene from other $C_4$ compounds, for example by distillation is, however, difficult and not efficient. One efficient method known from the prior art for separating isobutylene from other saturated and unsaturated $C_4$ compounds in cracker $C_4$ fraction is to react isobutylene with methanol to form methyl tert-butyl ether (MTBE), which is itself a valuable product, with use, for example, as an anti-knocking agent. The reaction to form MTBE is highly selective for isobutylene, thus facilitating a separation from other $C_4$ compounds. MTBE is then back-cracked ("split") to afford isobutylene and methanol. Isobutylene can also be obtained from splitting of ethyl tert-butyl ether (ETBE) to afford principally isobutylene and ethanol, together with side products.

An object of the present invention was to at least partially overcome some of the problems associated with the prior art.

Another object was to provide an economical, flexible process for producing methacrylic acid, methyl methacrylate and other esters thereof, from a $C_4$ feedstock comprising isobutylene and/or TBA.

A further object was to provide a process for producing methacrylic acid and esters thereof, including methyl methacrylate, where reactants can be recycled to as large an extent as possible, in particular to enable efficient and economical use of resources, without disadvantageously affecting the yield and/or quality of the products.

A particular object was to avoid the use of highly toxic chemicals in the production of methyl methacrylate.

A contribution to the solution of at least one of the above problems is made by the subject matter of the category-forming claims. The sub-claims dependent on the category-forming claims describe preferred embodiments according to the invention.

A contribution to the solution of the above objects is made by a process according 10 the present invention for preparation of methacrylic acid, comprising the steps:

a) providing a feed composition comprising at least one $C_4$ feed compound selected from isobutylene and tertiary butanol;
b) providing methanol;
c) subjecting the at least one $C_4$ feed compound and the methanol to a first catalytic reaction zone to obtain a reaction phase comprising methyl tertiary butyl ether;
d) separating at least a first part of methanol from the reaction phase to obtain a first methanol phase and a reaction phase depleted in methanol;
e) subjecting at least one of the reaction phase and the reaction phase depleted in methanol to a second catalytic reaction zone to obtain a splitting phase comprising isobutylene and methanol;
f) optionally separating at least a first part of isobutylene from the splitting phase to obtain a first isobutylene phase and a splitting phase depleted in isobutylene;
g) optionally subjecting at least one of the splitting phase and the first isobutylene phase to a first purification zone;
h) subjecting at least one of the optionally purified splitting phase and the optionally purified first isobutylene phase to a third catalytic reaction zone to obtain an oxidation phase comprising at least one $C_4$ oxidation product selected from methacrolein and methacrylic acid;
i) optionally subjecting the oxidation phase to a second purification zone.

A contribution to the solution of the above objects is made by a process according to the present invention for preparation of methyl methacrylate, comprising the steps:

a) providing a feed composition comprising at least one $C_4$ feed compound selected from isobutylene and tertiary butanol;
b) providing methanol;
c) subjecting the at least one $C_4$ feed compound and the methanol to a first catalytic reaction zone to obtain a reaction phase comprising methyl tertiary butyl ether;
d) separating at least a first part of methanol from the reaction phase to obtain a first methanol phase and a reaction phase depleted in methanol;
e) subjecting at least one of the reaction phase and the reaction phase depleted in methanol to a second catalytic reaction zone to obtain a splitting phase comprising isobutylene and methanol;
f) optionally separating at least a first part of isobutylene from the second reaction phase to obtain a first isobutylene phase and a splitting phase depleted in isobutylene;
g) optionally subjecting at least one of the splitting phase and the first isobutylene phase to a first purification zone;
h) subjecting at least one of the optionally purified splitting phase and the optionally purified first isobutylene phase to a third catalytic reaction zone to obtain an oxidation phase comprising at least one $C_4$ oxidation product selected from methacrolein and methacrylic acid;
i) optionally subjecting the oxidation phase to a second purification zone;
j) subjecting the optionally purified oxidation phase to a fourth catalytic reaction zone to obtain an esterification phase comprising methyl methacrylate;
k) optionally subjecting the esterification phase to a third purification zone.

The $C_4$ feed compound, preferably the isobutylene, comprised in the feed composition provided in step a) of the process according to the invention is preferably obtained from a cracking process, preferably a thermal or catalytic cracking process, preferably from a $C_4$ effluent from a cracker, preferably from a $C_4$ effluent from a steam cracker or from a fluid catalytic cracker. $C_4$ effluents from a cracker generally comprise a mix of olefinic $C_4$ compounds such as butadiene, isobutylene, 1-butene and 2-butene, as well as isomeric butanes. The cracker $C_4$ effluent is preferably subjected to at least one purification and/or separation step before being provided to the process according to the invention. For example, the cracker $C_4$ effluent can be subjected to an extraction or a hydrogenation, in particular a selective extraction or hydrogenation to remove or convert butadiene. The butadiene-depleted or butadiene-free raffinate resulting from a butadiene extraction or hydrogenation can then be used, for example, as feed composition in the process according to the invention. The feed composition then preferably comprises isobutylene, together with variable amounts of other $C_4$ compounds such as butanes, 1-butene, 2-butene. The feed composition preferably comprises at least 40 wt. %, preferably at least 50 wt. %, more preferably at least 60 wt. %, yet more preferably at least 70 wt. %, even more preferably at least 80 wt. %, more preferably at least 85 wt. %, more preferably at least 88 wt. %, more preferably at least 90 wt. %, yet more preferably at least 92 wt. % and even more preferably at least 95 wt. % isobutylene, based on the total amount of $C_4$ compounds in the feed composition. A preferred feed composition preferably comprises less than about 60 wt. %, preferably less than about 50 wt. %, preferably less than about 40 wt. %, yet more preferably less than about 30 wt. %, even more preferably less than about 20 wt. %, more preferably less than about 15 wt. %, more preferably less than about 12 wt. %, more preferably less than about 10 wt.-%, yet more preferably less than about 8 wt.-%, and even more preferably less than about 5 wt.-% $C_4$ compounds other than isobutylene, such as 1-butene, 2-butene and butane, based on the total amount of $C_4$ compounds in the feed composition.

Such a composition can be obtained, for example, directly as raffinate from the above-mentioned butadiene extraction, or after subjecting the butadiene-depleted or butadiene-free raffinate to a separation process, for example an extraction, a fractionation, a distillation, preferably a catalytic fractionation, a catalytic distillation or a reactive distillation, in order to obtain a product, preferably a top product in the case of fractionation or distillation, comprising isobutylene as main component together with variable amounts of other $C_4$ compounds, principally 1-butene and 2-butene. The bottom product of the separation process comprises mainly 2-butene, which can be subjected to an isomerisation process, for example an olefin metathesis process with ethylene, such as those available from the company ABB Lummus Global under the commercial name Olefins Conversion Technology (OCT). Such an isomerisation process has an additional advantage of providing a source of propylene.

If TBA is to be comprised as feed compound in the feed composition, this may be obtained commercially, prepared from isobutylene and water, for example from a source of isobutylene as described above, or alternatively obtained from propene oxide production via hydroperoxydation as described in U.S. Pat. No. 5,424,458, U.S. Pat. No. 5,436,376, U.S. Pat. No. 5,274,138, Ullmans encyclopedia, $5^{th}$ Edition, Vol. A4, p. 492 and references cited therein.

In step b) of the process according to the invention, methanol is provided. At least a part, or all, of the methanol can be provided from a commercial source of methanol, that is, methanol which is first introduced into the process according to the invention in this step. At least a part, or all, of the methanol provided in step b) can also be recycled to step b) from one or more process steps of the process according to the invention, for example as at least one methanol phase separated from the reaction phase in step d), step f) or step k) of the process according to the invention. It is preferred that at least a part of the methanol provided has been separated in step f) of the process according to the invention.

It is preferred in the process according to the invention that in step b) the methanol is provided in a molar excess, preferably a stoichiometric molar excess, compared to the at least one $C_4$ feed compound, preferably in a molar ratio of methanol:$C_4$ feed compound of 10:1 to 1:1, preferably 9:1 to 1:1, more preferably 8:1 to 1:1, more preferably 7:1 to 1:1, yet more preferably 6:1 to 1:1, more preferably 5:1 to 1:1, even more preferably 4:1 to 1:1, more preferably 3:1 to 1:1, more preferably 2:1 to 1:1, more preferably 1.5:1 to 1:1, more preferably 1.3:1 to 1:1, even more preferably 1.1:1 to 1:1, yet more preferably 1.05:1 to 1:1 and even more preferably 1.03:1 to 1:1, based on the number of moles of $C_4$ feed compound. A molar excess of methanol is preferred in order to increase the conversion of the at least one $C_4$ feed compound to MTBE in the first catalytic reaction zone. A greater excess results in increased formation of MTBE-methanol azeotrope.

In step c) of the process according to the invention the at least one $C_4$ feed compound and the methanol are subjected to a first catalytic reaction zone to obtain a reaction phase comprising MTBE. Exemplary reaction conditions, including suitable catalysts, temperatures and pressures for etherification of isobutylene with methanol to form MTBE are described, for example in A. Chauvel, G. Lefebvre, "Petrochemical Processes, Technical and Economic Characteristics", Vol. 1, Éditions Technip, Paris, 1989, p. 212-213, as well as in U.S. Pat. No. 4,665,237, U.S. Pat. No. 4,774,365, U.S. Pat. No. 4,299,999, U.S. Pat. No. 4,806,695, U.S. Pat. No. 4,906,788, U.S. Pat. No. 5,576,464, U.S. Pat. No. 4,570,026 and U.S. Pat. No. 5,336,841, among others. Exemplary reaction conditions, including suitable catalysts, temperatures and pressures for etherification of TBA with methanol to form MTBE are described, for example in EP 1 149 814 A1, WO 04/018393 A1, WO 04/052809 A1, U.S. Pat. No. 5,563,301, U.S. Pat. No. 5,243,091, U.S. Pat. No. 6,063,966, U.S. Pat. No. 5,856,588, U.S. Pat. No. 5,576,464, among others. The disclosures of these documents concerning preparation of MTBE are herewith incorporated by reference and form part of the disclosure of the present invention.

The effluent from the first catalytic reaction zone is preferably subjected to a purification and/or a separation, for example to at least one of a distillation, an extraction, an adsorption, an absorption, a chromatography, a washing, or the like, preferably to at least one of a distillation and an extraction, preferably to a distillation.

In step d) of the process according to the invention, at least a first part of methanol is separated from the reaction phase resulting from subjecting the feed composition to the first catalytic reaction zone, to obtain a first methanol phase and a reaction phase depleted in methanol. The methanol to be separated in this step is unreacted methanol which at least partially arises from the excess methanol provided in step b) of the process according to the invention. The methanol present in the reaction phase can also be present at least partially in the form of an azeotrope with MTBE. It is preferred according to the invention that at least 50%, preferably at least 60%, more preferably at least 70%, yet more preferably at least 80%, even more preferably at least 90%, more preferably at least 92%, yet more preferably at least 95%, more preferably at least 97%, even more preferably at least 98%, more preferably at least 99% and most preferably all of the methanol comprised in the reaction phase is separated from the reaction phase in step d). Suitable methods of separation are known to the skilled person and comprise, for example, distillation, adsorption, absorption, extraction, for example water extraction, separation using a membrane, pervaporation, phase separation azeoptropic distillation and the like. In particular, suitable methods are described in J. G. Stichlmair, J. R. Fair, "*Distillation: Principles and Practice*", Wiley-VCH, 2001, (p. 238 for azeotropic distillation), H. Z. Kister, "*Distillation Design*", McGraw-Hill Professional, 1$^{st}$ edition, 1992 and H. Z. Kister, "*Distillation Operation*", McGraw-Hill Professional, 1$^{st}$ edition, 1990 and in DE 102 38 370, as well as in the references mentioned above with respect to the preparation of MTBE, in particular in U.S. Pat. No. 5,336,841, U.S. Pat. No. 4,665,237, U.S. Pat. No. 4,774,365, U.S. Pat. No. 4,299,999, U.S. Pat. No. 5,243,091. The disclosures of these documents concerning separation of methanol from a reaction phase arising from production of MTBE are herewith incorporated by reference and form part of the disclosure of the present invention.

The first methanol phase can be subjected to purification, for example to remove water or other undesired components comprised therein. Suitable methods of purification are well known to the person skilled in the art and comprise, for example, distillation, rectification, chromatography, washing, extraction, absorption, adsorption, drying and the like.

In a preferred embodiment of the process according to the invention, at least a part, preferably at least 50%, preferably at least 60%, more preferably at least 70%, even more preferably at least 80%, yet more preferably at least 85%, more preferably at least 90%, even more preferably at least 92%, yet more preferably at least 95%, more preferably at least 97%, even more preferably at least 98%, more preferably at least 99%, more preferably all of the methanol comprised in the optionally purified first methanol phase, based on the methanol in the first methanol phase, is provided to the fourth catalytic reaction zone.

The amount of methanol to be provided to the fourth catalytic reaction zone from the first methanol phase depends on the amount of methanol required for the esterification and thus on the amount of methacrylic acid conducted to the fourth catalytic reaction zone, as well as on the amount of methanol present in the first methanol phase.

It is possible according to the process according to the invention that MTBE arising from the first catalytic reaction zone and MTBE from another source, for example commercial MTBE, are combined and a combined MTBE phase is supplied to the second catalytic reaction zone for splitting. MTBE arising from the first catalytic reaction zone and MTBE obtainable from a commercial source can differ from each other in their exact composition, in particular in their composition of impurities. This MTBE mixing can be advantageous, for example depending on the respective availabilities and prices of different feedstocks such as cracker $C_4$ effluents and raffinates thereof and MTBE.

If, in the process according to the invention, MTBE from a source other than the first catalytic reaction zone is to be provided to the second catalytic reaction zone, the amount of methanol in the first methanol phase may not be sufficient for esterification of the total amount of methacrylic acid and/or methacrolein in the fourth catalytic reaction zone, if the total amount of methacrylic acid and/or methacrolein is to be subjected to the fourth catalytic reaction zone. It may, therefore, be necessary additionally to provide methanol from one or more further methanol sources.

In step e) of the process according to the invention, at least one of the reaction phase and the reaction phase depleted in methanol, preferably the reaction phase depleted in methanol, preferably the methanol-free reaction phase, is subjected to a second catalytic reaction zone to obtain a splitting phase comprising isobutylene and methanol. Such splitting of MTBE, preferably catalytic splitting of MTBE, is well known in the art and can occur by any suitable means known to the skilled person. Suitable catalysts and reaction conditions are described, for example, in EP 1 149 814 A1, WO 04/018393 A1, WO 04/052809 A1; Ullmann's Encyclopedia of Industrial Chemistry, 5$^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, 5$^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein. The disclosures of these references are hereby incorporated by reference and form part of the disclosure of the present invention.

Further components are often also present in the splitting phase resulting from the MTBE splitting, such as, among others, dimethyl ether, tert-butyl alcohol, methyl sec-butyl ether (MSBE) and unreacted MTBE. Accordingly, in a preferred aspect of the process according to the invention, the splitting phase is subjected to at least one of separation and purification before being used in a subsequent process step. It is preferred that in an optional process step f), at least a first part of isobutylene from the splitting phase is separated to obtain a first isobutylene phase and a splitting phase depleted in isobutylene. Suitable processes are described, for example, in EP 1 149 814 A1, WO 04/018393 A1, WO 04/052809 A1.

It is preferred according to the invention that the ratio of isobutylene to other $C_4$ hydrocarbons is increased in the first isobutylene phase compared to the feed composition. By an increased ratio of isobutylene to other $C_4$ hydrocarbons in the first isobutylene phase compared to the feed composition is meant that the first isobutylene phase is depleted in other $C_4$ hydrocarbons, in particular other unsaturated $C_4$ hydrocarbons, compared to the feed composition The first isobutylene phase, optionally purified in step g) of the process according to the invention as described below, preferably comprises at least 90 wt. % isobutylene, preferably at least 91 wt. % isobutylene, more preferably at least 92 wt. % isobutylene, more preferably at least 93 wt. % isobutylene, yet more preferably at least 94 wt. % isobutylene, even more preferably at least 95 wt. % isobutylene more preferably at least 96 wt. % isobutylene, yet more preferably at least 97 wt. % isobutylene, even more preferably at least 98 wt. % isobutylene, more preferably at least 99 wt. % isobutylene, even more preferably at least 99.5 wt. % isobutylene, yet more preferably at least 99.7 wt. % isobutylene, more preferably at least 99.9 wt. % isobutylene, based on the total weight of the hydrocarbons in the optionally purified first isobutylene phase.

In a further preferred aspect of step f) of the process according to the invention, at least a part of the methanol formed in step e) is separated from the splitting phase as a second methanol phase Suitable processes are described, for example, in EP 1 149 814 A1, WO 04/018393 A1 and WO 04/052809 A1. The second methanol phase can be optionally purified as described above, and provided to at least one of steps b), c) or j) of the process according to the invention, preferably to at least one of the first catalytic reaction zone and the fourth catalytic reaction zone.

In step g) of the process according to the invention at least one of the splitting phase and the first isobutylene phase, preferably the first isobutylene phase, is optionally subjected to a first purification zone. Suitable purification methods are known to the person skilled in the art and preferably comprise at least one of distillation, extraction, adsorption, absorption, chromatography or washing, preferably at least one of distillation and extraction, preferably at least one distillation and at least one extraction. It is preferred that in this process step at least one of methanol and MTBE is at least partially separated from at least one of the splitting phase and the first isobutylene phase, preferably from the first isobutylene phase. The separated methanol can be optionally purified and at least partially recycled to step b) or provided to the fourth catalytic reaction zone. Separated MTBE can be optionally purified and at least partially recycled to the second catalytic reaction zone.

In step h) of the process according to the invention at least one of the optionally purified splitting phase and the optionally purified first isobutylene phase is subjected to a third catalytic reaction zone to obtain an oxidation phase comprising at least one $C_4$ oxidation product selected from methacrolein and methacrylic acid. It is thus preferred that in step h) of the process according to the invention at least a part of the isobutylene phase is subjected to oxidation.

In a preferred embodiment of the process according to the invention, the oxidation in step h) takes place in a single oxidation stage. If the process according to the invention comprises a single oxidation stage in step h), it is preferred that the resulting oxidation phase comprises methacrylic acid as main component.

In another preferred embodiment of the process according to the invention, the oxidation in step h) takes place in at least two separate oxidation stages, preferably in two separate oxidation stages. These at least two oxidation stages can be oxidation stages within a same area of the catalytic reaction zone, for example if the catalytic reaction zone is in the form of one or more reactors, a first oxidation stage can be in a first oxidation area in a reactor and a further oxidation stage can be in a further oxidation area downstream of the first oxidation area in the same reactor, or a first oxidation stage can be in a first reactor and a further oxidation stage can be in a further reactor. It is preferred that the first oxidation stage and the further oxidation stage are at different temperatures, and preferably that the first oxidation stage and the further oxidation stage are separated by an intermediate area at a different temperature to that of either of the first and further oxidation stages.

In an embodiment of the process according to the invention wherein in step b) the oxidation takes place in two separate oxidation stages, it is possible that one or both of the oxidation stages are gas phase or liquid phase oxidation stages. It is also possible that one oxidation stage is a gas phase oxidation stage and the other oxidation stage is a liquid phase oxidation stage. In a preferred aspect of the process according to the invention, the first and second oxidation stages are gas phase oxidation stages. In another preferred aspect of the process according to the invention, the first oxidation stage is a gas phase oxidation stage and the second oxidation stage is a liquid phase oxidation stage. If the second oxidation stage is a liquid phase oxidation stage it is also possible that this second oxidation stage is combined with step j) into a combined liquid phase oxidation-esterification stage.

In an embodiment of the process according to the invention where the oxidation takes place in at least two separate oxidation stages, it is possible that a quenching step takes place between at least two of the at least two separate oxidation stages. This quenching step is preferably a quenching step enabling isolation of methacrolein. This embodiment can be particularly preferred if a second or further oxidation stage is a liquid phase oxidation stage, or if a second or further oxidation stage is combined with step j) into a combined liquid phase oxidation-esterification stage. Quenching of this type can be carried out by any suitable method known to the skilled person. Suitable methods are described, for example, in DE 34 41 207 A1 and in JP 60087241.

To the optionally purified splitting phase or to the optionally purified first isobutylene, preferably to the optionally purified first isobutylene phase is preferably added in step h) a source of oxygen, which source is not limited and which can be any suitable source of oxygen ($O_2$) such as peroxide, molecular oxygen or oxygen-enriched or oxygen-comprising gas, whereby air is preferred as oxygen source for economic reasons. An $O_2$ source is understood here to be any compound or composition that comprises or liberates $O_2$. The amount of molecular oxygen provided as $O_2$ or as $O_2$ source is preferably from about 0.5 to about 20 moles, preferably from about 1 to about 10 moles $O_2$ per mole of isobutylene and/or TBA, more preferably from about 1 to about 5 moles $O_2$ per mole of isobutylene and/or TBA, more preferably from about 1 to about 3 moles $O_2$ per mole of isobutylene and/or TBA, more preferably from about 1 to about 2 moles $O_2$ per mole of isobutylene and/or TBA. Water and/or water vapour can also be added to the feed composition. If water and/or water vapour is added to the feed composition it is preferred that from about 1 to about 20 moles, preferably from about 1 to about 15 moles, preferably from about 1 to about 10 moles, more preferably from about 1 to about 8 moles of water and/or water vapour is added to the feed composition, based on the number of moles of isobutylene and/or TBA. It may not be preferred to add water and/or water vapour to the isobutylene phase in step h) to the extent that TBA is comprised therein. It is further preferred that at least one diluent is added to the isobutylene phase, which diluent can comprise inorganic or organic solvent or a gas, preferably at least one diluent gas which is inert under the reaction conditions, preferably selected from nitrogen, argon and carbon dioxide, whereby nitrogen gas and/or carbon dioxide, preferably carbon dioxide recycled from a catalytic or thermal combustion unit, preferably from a catalytic combustion unit, is preferred as diluent gas.

In an aspect of the process according to the invention comprising a two-stage oxidation, it is preferred that in a first oxidation stage the amount of $O_2$ provided is preferably from about 0.5 to about 10 moles, preferably from about 1 to about 5 moles, more preferably from about 1 to about 3 moles, more preferably from about 1 to about 2 moles $O_2$ per mole of isobutylene and/or TBA, and a preferred amount of water and/or water vapour is in the range from 0 to about 20 moles, preferably from 0 to about 10 moles, more preferably from 0 to about 5 moles $H_2O$ per mole of isobutylene and/or TBA, whereby a molar ratio $O_2$:isobutylene and/or TBA:water and/or water vapour of about 2:1:1 is preferred. In a second oxidation stage the amount of $O_2$ provided is preferably from about 0.5 to about 10 moles, preferably from about 1 to about 5 moles, more preferably from about 1 to about 3 moles $O_2$ per mole of isobutylene and/or TBA, and a preferred amount of water and/or water vapour is in the range from about 1 to about 20 moles, preferably from about 1 to about 10 moles, more preferably from about 2 to about 8 moles $H_2O$ per mole of isobutylene and/or TBA, whereby a preferred molar ratio $O_2$:isobutylene and/or TBA:water and/or water vapour in a second oxidation stage is in the range of about 2:1:2-6, preferably in the range of about 2:1:3-5, based on the number of moles isobutylene and/or TBA comprised in the isobutylene phase.

If step h) of the process according to the invention takes place in at least two separate oxidation stages, it is preferred that the main product of a first oxidation stage is methacrolein and the main product of a further oxidation stage is methacrylic acid. A polymerisation inhibitor is preferably added to methacrylic acid, so that manipulation of methacrylic acid in at least one process step, in particular in any process step taking place at increased temperature, preferably takes place in the presence of a polymerisation inhibitor.

The oxidation phase exiting the catalytic reaction zone is preferably subjected to at least one of quenching and/or purification to isolate methacrylic acid and to remove unreacted compounds and/or methacrolein and/or undesired side products arising from the reaction or reactions in the catalytic reaction zone.

In step i) of the process according to the invention, the oxidation phase can be subjected to a second purification zone, preferably a purification zone for methacrylic aid. Purification in step i) can be carried out by any suitable purification means known to the skilled person, such as by distillation, crystallisation, extraction, absorption or precipitation, preferably by crystallisation. Such purification techniques are well known in the art, for example in JP 01193240, JP 01242547, JP 01006233, DE 100 39 025 A1, US 2003/0175159, DE 100 36 881 A1, EP 297 445 A2, U.S. Pat. No. 6,596,901 B1, U.S. Pat. No. 6,646,161 B1, U.S. Pat. No. 5,248,819, U.S. Pat. No. 4,618,709 B1, and references cited therein. Reference is hereby explicitly made to these disclosures concerning purification and they form part of the disclosure of the present invention.

If step h) occurs at least partially in the gas phase, it is preferred that a quenching step as described above is carried out prior to a purification of the oxidation phase.

A quenching can be carried out by any suitable quenching process known to the skilled person, as described for example in Offenlegungsschrift DE 21 36 396, EP 297 445 A2, EP 297 788 A2, JP 01193240, JP 01242547, JP 01006233, US 2001/0007043 A1, U.S. Pat. No. 6,596,901 B1, U.S. Pat. No. 4,956,493, U.S. Pat. No. 4,618,709 B1, U.S. Pat. No. 5,248,819, whose disclosure concerning quenching of acrylic and methacrylic acids is hereby incorporated and forms part of the present disclosure. Preferred quenching agents are water and organic solvents such as, for example, aromatic or aliphatic hydrocarbons, or mixtures of at least two thereof, whereby preferred organic solvents have relatively low vapour pressure under the quenching conditions, such as heptane, toluene or xylene.

It is preferred that in a quenching step and/or in a purification step methacrolein is separated. The separated methacrolein can be recycled to the catalytic reaction zone, whereby if the catalytic reaction zone comprises more than one oxidation stage the separated methacrolein is preferably recycled to a further oxidation stage, preferably to the second oxidation stage of a catalytic reaction zone comprising two oxidation stages. In this way, the separated methacrolein can be further subjected to oxidation, thereby leading to increased efficiency of the overall process and increased yields of methacrylic acid and methyl methacrylate.

Methacrylic acid produced in steps a) to i) above can be at least partially collected, or it can be conducted to further reactions or processes. At least one polymerisation inhibitor is preferably added to the methacrylic acid. Typical yields of methacrylic acid obtainable by the process according to the invention are in the range from about 50% to about 80%, based on isobutylene and/or TBA in the phase subjected to the oxidation, whereby yields of about 55% to about 75% are generally obtained.

In step j) of the process according to the invention for preparation of methyl methacrylate, the generally optionally but in some cases necessarily quenched and/or purified oxidation phase is subjected to a fourth catalytic reaction zone to obtain an esterification phase comprising methyl methacrylate.

Methanol is also provided to the fourth catalytic reaction zone according to the process according to the invention, preferably in excess, for example an excess of from about 0.5 to about 10 mol %, preferably from about 0.6 to about 5 mol %, more preferably from about 1 to about 2 mol %, based on the amount of oxidation phase subjected to the fourth catalytic reaction zone, preferably based on the number of moles of methacrylic acid and/or methacrolein subjected to the fourth catalytic reaction zone. It is preferred according to the invention that the methanol is methanol which has been separated, in step d) of the process according to the invention, from the reaction phase resulting from the first catalytic reaction zone. It is also possible to add methanol from another source, whereby it is preferred to combine this methanol with at least a part of the methanol separated in step d) of the process according to the invention. Other possible sources of methanol are methanol separated in other process steps according to the invention, for example from step f) or step k), as well as commercially obtainable methanol. Addition of methanol from another source is preferred if the amount of methanol separated in step d) of the process according to the invention is less than the amount desired for as complete as possible an esterification in step j) of the process according to the invention.

The means of carrying out the esterification in step j) of the process according to the invention is not particularly limited. The esterification can be carried out, for example, as described in U.S. Pat. No. 6,469,292, JP 1249743, EP 1 254 887 A1, U.S. Pat. No. 4,748,238, U.S. Pat. No. 4,474,981, U.S. Pat. No. 4,956,493 or U.S. Pat. No. 4,464,229 whose disclosures concerning esterification of acrylic and methacrylic acids are hereby incorporated and form part of the present disclosure. The esterification is preferably catalysed by an acidic catalyst or by a catalyst comprising acidic groups, preferably by a solid state catalyst comprising acidic groups. An oxyesterification is also possible, for example as described in the literature cited above. The esterification or the oxyesterification preferably takes place in the presence of a polymerisation inhibitor to prevent polymerisation of methacrylic acid and/or methyl methacrylate.

In step k) of the process according to the invention for preparation of methyl methacrylate, the esterification phase is optionally subjected to a third purification zone. In step k), preferably methyl methacrylate is separated from other esterification phase components such as unreacted methanol and/or methacrylic acid and other impurities. Suitable purification methods are known to the person skilled in the art and preferably comprise at least one of distillation, crystallisation, extraction, chromatography or washing more preferably at least one distillation device. Separated methanol and/or methacrylic acid can be recycled to other reaction steps, or to the esterification step, optionally after purification. Methanol is preferably recycled to at least one of steps b), c), f) and j).

It is preferred in the processes according to the invention that at least step h), preferably at least one, more preferably both oxidation stages of a two-stage oxidation in step h), occurs at least partially in the gas phase. It is also possible that other process steps occur at least partially in the gas phase, whereby preferably at least one of steps c), e) and j) also occurs at least partially in the gas phase. It is also conceivable that at least one or even all process steps occur at least partially in liquid phase. Thus it is possible that all steps occur at least partially in liquid phase, that all steps occur at least partially in the gas phase, or that at least one step occurs at least partially in the liquid phase and the remaining step or steps occur at least partially in the gas phase. If step j) is combined with a second oxidation stage of step h) into an oxidation-esterification step, it is preferred that the oxidation-esterification step occurs in liquid phase and, accordingly, that the second oxidation stage likewise occurs in liquid phase.

A further contribution to solving the above problems is made by an apparatus for production of methacrylic acid, comprising i) at least one supply for at least one $C_4$ feed compound and at least one supply for methanol, each supply being in fluid communication with
ii) a first catalytic reaction zone for at least partial conversion of the feed composition into MTBE; in fluid communication with
iii) at least one first separation unit for separation of methanol from the effluent of the first catalytic reaction zone; in fluid communication with
iv) a mixing unit; in fluid communication with
v) a second catalytic reaction zone for at least partial splitting of MTBE; in fluid communication with
vi) at least one second separation unit for separation of a first isobutylene phase from the effluent of the second catalytic reaction zone; in fluid communication with
vii) a third catalytic reaction zone for at least partial oxidation of the first isobutylene phase to an oxidation phase comprising at least one $C_4$ oxidation product selected from methacrolein and methacrylic acid.

A further contribution to solving the above problems is made by an apparatus for production of methyl methacrylate, comprising i) at least one supply for at least one $C_4$ feed compound and at least one supply for methanol, each supply being in fluid communication with
ii) a first catalytic reaction zone for at least partial conversion of the feed composition into MTBE; in fluid communication with
iii) at least one first separation unit for separation of methanol from the effluent of the first catalytic reaction zone; in fluid communication with
iv) a mixing unit; in fluid communication with
v) a second catalytic reaction zone for at least partial splitting of MTBE; in fluid communication with
vi) at least one second separation unit for separation of a first isobutylene phase from the effluent of the second catalytic reaction zone; in fluid communication with
vii) a third catalytic reaction zone for at least partial oxidation of the first isobutylene phase to an oxidation phase comprising at least one $C_4$ oxidation product selected from methacrolein and methacrylic acid; in fluid communication with
viii) a fourth catalytic reaction zone for esterification of at least one component of the oxidation phase; in fluid communication with
ix) a supply for methanol, in fluid communication with the at least one first separation unit.

The term "in fluid communication" is understood here as meaning that a fluid, which can be at least one of a liquid, a gas, a vapour, a supercritical fluid or any other fluid, can flow from one area or component to another with which the former is in fluid communication.

Any supply which is intended to supply a gaseous phase or composition is preferably maintained at a temperature above the dewpoint temperature of the gas to be supplied. This can be achieved, for example, by heating or by thermally insulating the supply.

The at least one supply for at least one $C_4$ feed compound is preferably at least one supply for at least one of isobutylene and TBA.

Each supply can be any means suitable for supplying respectively at least one $C_4$ feed compound and methanol to the first catalytic reaction zone, for example a reservoir, a pipe, a line, a tube, or the like. In particular, the supply is preferably resistant to elevated and/or decreased temperature and/or pressure.

A good temperature and/or pressure resistance is particularly preferred if one or more of the reactions which should take place in the apparatus according to the invention is a gas phase reaction. The supply is furthermore preferably not reactive with any of the components of the feed composition, nor with any further component or components which might be added to the feed composition, as mentioned above in connection with the process according to the invention.

In a preferred aspect of the apparatus according to the invention, the at least one supply for the at least one $C_4$ feed compound is in fluid communication with a cracker, preferably with a $C_4$ outlet of a cracker. The cracker is preferably a thermal or catalytic cracker, preferably a steam cracker or a fluid catalytic cracker. At least one purification and/or separation unit is preferably located downstream of the cracker so that the cracker $C_4$ effluent can be at least partially purified before being conducted to the at least one supply for at least one $C_4$ feed compound. The at least one purification and/or separation unit can comprise an extraction unit or a hydrogenation unit, for example a selective extraction or hydrogenation unit which removes or converts butadiene. The at least one purification and/or separation unit preferably further comprises a unit suitable for separating a product comprising isobutylene as main component, optionally together with variable amounts of other $C_4$ compounds, principally 1-butene and 2-butene. Such a unit can be, for example, an extraction unit, a fractionation unit, a distillation unit, preferably a catalytic fractionation unit, a catalytic distillation unit or a reactive distillation unit. An isomerisation reactor may further be in fluid communication with the at least one purification and/or separation unit, preferably an olefin metathesis reactor such as those available from the company ABB Lummus Global under the commercial name Olefins Conversion Technology (OCT). The at least one purification and/or separation unit preferably also separates a composition comprising 2-butene as main component, which is supplied to the isomerisation reactor, if present. Such an isomerisation reactor has an additional advantage of providing a source of valuable propylene by conversion of less valuable 2-butene with ethylene into propylene and conversion of 1-butene into 2-butene.

The apparatus according to the invention also comprises at least one supply for methanol. The methanol supply is in fluid communication with a methanol source, such as a methanol reservoir or a source of recycled methanol, whereby a preferred source of recycled methanol is at least one of the components of the apparatus according to the invention where methanol is at least partially separated.

Each of the above supplies is in fluid communication with a first catalytic reaction zone for at least partial conversion of the feed composition into MTBE. Exemplary reactors and reaction conditions, including suitable catalysts, temperatures and pressures for etherification of isobutylene with methanol to form MTBE are known to the skilled person and are described in the references given above in connection with the disclosure of the process step for formation of MTBE, for example in A. Chauvel, G. Lefebvre, "Petrochemical Processes, Technical and Economic Characteristics", Vol. 1, Éditions Technip, Paris, 1989, p. 212-213; Ullmann's Encyclopedia of Industrial Chemistry, $5^{th}$ Edition, Volume A16, p. 543-550, as well as in U.S. Pat. No. 4,665,237, U.S. Pat. No. 4,774,365, U.S. Pat. No. 4,299,999, U.S. Pat. No. 4,806,695, U.S. Pat. No. 4,906,788, U.S. Pat. No. 5,576,464, U.S. Pat. No. 4,570,026 and U.S. Pat. No. 5,336,841, among others. Etherification of TBA with methanol to form MTBE is described, for example in EP 1 149 814 A1, WO 04/018393 A1, WO 04/052809 A1, U.S. Pat. No. 5,563,301, U.S. Pat. No. 5,243,091, U.S. Pat. No. 6,063,966, U.S. Pat. No. 5,856,588, U.S. Pat. No. 5,576,464, among others. The disclosures of these documents concerning preparation of MTBE are herewith incorporated by reference and form part of the disclosure of the present invention.

The first catalytic reaction zone is preferably in fluid communication with at least one first separation unit for separation of methanol from the effluent of the first catalytic reaction zone. The separation unit can comprise any means suitable and known to the skilled person for separating methanol from the other components comprised in the effluent of the first catalytic reaction zone. Examples of suitable means are an extractor, a crystalliser, a column, a distillation device, a rectification device, a membrane, a pervaporation device, a phase separation device, an absorption device, an adsorption device and a wash device.

The at least one first separation unit is preferably in fluid communication with a mixing unit. The mixing unit comprises at least two inlets for MTBE, preferably a first inlet for MTBE arising from the first catalytic reaction zone and a second inlet for MTBE from another source, for example for commercial MTBE. In the mixing unit MTBE entering via the first and second inlets can be combined. The combined MTBE phase can then be supplied to the second catalytic reaction zone.

The mixing unit is thus preferably in fluid communication with a second catalytic reaction zone for at least partial splitting of MTBE. Splitting units and suitable catalysts for MTBE splitting are well known in the art and form part of the general knowledge of the skilled person, as described, for example, in Ullmann's Encyclopedia of Industrial Chemistry, $5^{th}$ Edition, Vol. A4, p. 488; V. Fattore, M. Massi Mauri, G. Oriani, G. Paret, Hydrocarbon Processing, August 1981, p. 101-106; Ullmann's Encyclopedia of Industrial Chemistry, $5^{th}$ Edition, Vol. A16, p. 543-550; A. Chauvel, G. Lefebvre, "Petrochemical Processes, Technical and Economic Characteristics", Vol. 1, Éditions Technip, Paris, 1989, p. 213 et seq.; U.S. Pat. No. 5,336,841, U.S. Pat. No. 4,570,026, and references cited therein.

The second catalytic reaction zone is in fluid communication with at least one second separation unit for separation of a first isobutylene phase from the effluent of the second catalytic reaction zone. The separation unit can be at least one of an extractor, a crystalliser, a column, a distillation device, a rectification device, a membrane, a pervaporation device and a wash device.

It is preferred in the apparatus according to the invention that the at least one second separation unit comprises an outlet for a second methanol phase. The at least one second separation unit can further comprise a methanol separation unit, for example at least one of an extractor, a crystalliser, a column, a distillation device, a rectification device, a membrane, a pervaporation device, an adsorption unit, an absorption unit and a wash device, or the methanol can be separated in the separation unit for separation of an isobutylene phase.

The at least one second separation unit is preferably in fluid communication with a third catalytic reaction zone for at least partial oxidation of the isobutylene phase to an oxidation phase comprising at least one $C_4$ oxidation product selected from methacrolein and methacrylic acid.

In the apparatus according to the invention, the third catalytic reaction zone preferably comprises at least one oxidation unit. The at least one oxidation unit is preferably at least one oxidation unit suitable for carrying out oxidation of isobutylene and/or TBA to at least one of methacrolein and methacrylic acid, preferably comprising at least one oxidation catalyst. The at least one oxidation unit can be, for example, a multitube reactor such as a tube and shell reactor, a plate reactor or a fluidised bed reactor, whereby a multitube reactor is preferred, preferably a multitube reactor packed with oxidation catalyst. Such reactors are commercially available, for example from MAN DWE GmbH, Deggendorfer Werft, Germany, or from Ishikawajima-Harima Heavy Industries (IHI Corporation from 1 Jul. 2007), Japan, and form part of the general knowledge of the person skilled in the art.

In a preferred embodiment of the apparatus according to the invention, the catalytic reaction zone comprises one oxidation area, preferably one oxidation unit, whereby it is preferred that this oxidation area comprises at least one catalyst, preferably one catalyst, preferably a catalyst capable of oxidation of at least one of isobutylene and TBA to at least one of methacrolein and methacrylic acid, preferably to methacrylic acid.

In another preferred embodiment of the apparatus according to the invention, it is preferred that the third catalytic reaction zone comprises at least a first oxidation area and a further oxidation area, preferably a first oxidation area and a second oxidation area. The first oxidation area and the further oxidation area, preferably the first oxidation area and the second oxidation area, can be different oxidation areas in a single reactor, or they can each be in a separate respective reactor, with all reactors being in fluid communication with each other. In an embodiment where the catalytic reaction zone is in the form of one reactor, a first oxidation stage is preferably in a first oxidation area in a reactor and a further oxidation stage is then in a further oxidation area downstream of the first oxidation area in the same reactor. It is preferred that the reactor is a multitube reactor as described above. In this case it is preferred that at least one oxidation catalyst, preferably at least two oxidation catalysts, are provided, preferably in a layered-type fashion, preferably such that a first oxidation stage occurs at at least one upstream catalyst layer and a further oxidation stage at at least one further catalyst layer downstream thereof. Catalyst layers in a same tube can be directly adjacent to each other. It is also possible that at least one catalyst layer is separated from at least one other catalyst layer by at least one intermediate area, for example at least one mixing area or at least one transition area, e.g. at least one transition area between an area with a certain number of tubes and an area with a different number of tubes, or by means of layers of, for example, packing materials or suspending agents which are inert under the reaction conditions. If, in a process where the first oxidation and a further oxidation occur in the gas phase, the first oxidation area and the further oxidation area are in separate reactors, it is preferred that all reactors are multitube reactors. On the other hand, if at least one reactor is a liquid phase reactor, for example a liquid phase oxyesterification reactor, this reactor is preferably not a multitube reactor.

It is preferred that the first oxidation area and the further oxidation area or areas are at different temperatures. It is further preferred that the first and further oxidation areas are separated by an intermediate area which is at a different temperature to that of either of the first and further oxidation stages.

In a preferred aspect of the apparatus according to the invention the at least one oxidation unit thus comprises at least one catalyst layer of at least one oxidation catalyst.

It is preferred in the apparatus according to the invention that, if the apparatus comprises a first oxidation area and a further oxidation area in the third catalytic reaction zone, the first oxidation area comprises a first oxidation catalyst and the further oxidation area comprises a further oxidation catalyst, whereby the further oxidation area is preferably a second oxidation area and the further oxidation catalyst is preferably a second oxidation catalyst. The first oxidation catalyst is preferably a catalyst for oxidation of isobutylene to methacrolein, and the further oxidation catalyst, preferably the second oxidation catalyst, is preferably a catalyst for oxidation of methacrolein to methacrylic acid. The first and further catalysts are not particularly limited and are preferably solid catalysts suitable for the oxidation, preferably mixed metal oxide catalysts. Such catalysts are well known in the art, for example as described in US 2002/0198406 A1, EP 911 313 A1, U.S. Pat. No. 5,602,280, EP 145 469 A2, U.S. Pat. No. 5,218,146, U.S. Pat. No. 4,365,087, U.S. Pat. No. 5,077,434, U.S. Pat. No. 5,231,226 or US 2003/0004374 A1, U.S. Pat. No. 6,498,270 B1, U.S. Pat. No. 5,198,579, EP 1 595 600 A1, EP 1 052 016 A2, U.S. Pat. No. 5,583,084, and references cited therein, whose disclosure concerning oxidation catalysts is hereby incorporated by reference and forms a part of the disclosure of the present invention. If a first and a further oxidation catalyst are comprised they are preferably arranged in the at least one oxidation area as described above.

In a preferred aspect of the apparatus of the present invention, at least one supply for at least one $O_2$ source, preferably at least one supply for air, and at least one supply for water and/or steam, are in fluid communication with at least one of the catalytic reaction zone and the supply. It is preferred according to the invention that the at least one supply for at least one $O_2$ source and the at least one supply for water and/or steam provide respectively at least one $O_2$ source and water and/or steam directly to the catalytic reaction zone. If the catalytic reaction zone comprises at least a first and a further oxidation area, the apparatus preferably comprises at least one supply for at least one $O_2$ source and at least one supply for water and/or steam for each oxidation area. The apparatus can further comprise a supply for a diluent such as nitrogen, argon, carbon dioxide, a saturated hydrocarbon, a combustion gas or the like, preferably nitrogen or carbon dioxide, preferably recycle gas comprising at least carbon dioxide recycled from a catalytic combustion unit (CCU) or a thermal combustion unit (TCU).

If the apparatus according to the invention comprises a first oxidation reactor and at least one further oxidation reactor as described above, it is possible that a quenching unit is provided after the first oxidation reactor and before at least one further oxidation reactor, preferably between the first and second oxidation reactors. This quenching unit preferably serves to isolate methacrolein. A quenching unit between the first oxidation reactor and at least one further oxidation reactor is preferred if the first oxidation reactor is a gas phase reactor and the at least one further reactor is a liquid phase reactor. Quenching units suitable for use in the apparatus are preferably those as described, for example, in the references cited above in connection with a quenching process step, in particular with an intermediate quenching step between two oxidation stages.

The apparatus according to the invention optionally comprises at least one second purification unit, downstream of and in fluid communication with the third catalytic reaction zone. In the apparatus for production of methyl methacrylate, the at least one second purification unit is upstream of the esterification unit. The at least one second purification unit is preferably suitable for purification of methacrylic acid, preferably for separation of methacrylic acid from water and/or terephthalic acid (TPA), and preferably comprises at least one of a distiller, a crystalliser, an extractor, a wash device and a column. It is particularly preferred that the at least one second purification unit comprises at least one crystalliser. It is possible that the at least one second purification unit comprises more than one purification stage. Unreacted methacrolein can be separated here and, if desired, conducted back to the catalytic reaction zone for further reaction. Suitable purification units are described in the references cited above in connection with a process step for purification of methacrylic acid.

In a preferred embodiment of the apparatus according to the invention, at least one quench unit is comprised between and in fluid communication with the catalytic reaction zone and the purification unit. It is preferred that methacrylic acid present in the oxidation phase leaving the catalytic reaction zone is condensed in the quench unit to form a solution comprising methacrylic acid as main oxidation product. Unreacted methacrolein can also be separated in the quench unit and, if desired, conducted back to the catalytic reaction zone for further reaction. Quench units suitable for use in the apparatus according to the invention are described, for example, in the references cited above in connection with a quenching process step.

In the apparatus for production of methyl methacrylate, the third catalytic reaction zone, preferably via at least one of a quench unit and a purification unit as described above, is preferably in fluid communication with a fourth catalytic reaction zone for esterification of at least one component of the oxidation phase.

The esterification unit is not particularly limited and can be any unit suitable for esterification to form methyl methacrylate. It is preferably suitable for liquid phase esterification. The esterification unit preferably comprises an esterification catalyst, which can be a heterogeneous or homogeneous catalyst such as a solid state catalyst or a liquid catalyst, and is preferably an acidic ion exchange resin such as those described in U.S. Pat. No. 6,469,202, JP 1249743, EP 1 254 887 A1 or commercially available under the trade names Amberlyst® (Rohm and Haas Corp.), Dowex®, (Dow Corp.) or Lewertit® (Lanxess AG), or an acid capable of catalysing esterification, such as sulphuric acid, $H_2SO_4$.

The fourth catalytic reaction zone according to the invention is preferably in fluid communication with a supply for methanol, the supply for methanol preferably being in fluid communication with the at least one first separation unit. The supply for methanol preferably comprises a purification unit for methanol downstream of the fourth catalytic reaction zone. Suitable purification units are known to the person skilled in the art and preferably comprise at least one distillation device, crystalliser, extractor, column or wash device, more preferably at least one distillation device. An example of a purification unit for methanol is described in EP 1 254 887 A1. The supply for methanol can also be in fluid communication with at least one of the second separation unit, the first purification unit, and a source of methanol, which can be commercially obtained methanol or, for example, recycled methanol, for example methanol recycled from the esterification in the fourth catalytic reaction zone.

The apparatus may further comprise at least one third purification unit downstream of the esterification unit, for purification of methyl methacrylate. Suitable purification units are known to the person skilled in the art and preferably comprise at least one distillation device, crystalliser, extractor, column or wash device, more preferably at least one distillation device. The at least one third purification unit should enable the at least partial purification of methyl methacrylate and at least partial separation of side products, for example impurities arising from the esterification, unreacted methanol and/or unreacted methacrylic acid. Unreacted reagents can optionally be recycled into the esterification reaction, optionally after being subjected to purification, or can be conducted away.

Each supply comprised in the apparatus according to the invention can be any means suitable for supplying respectively the desired feedstock to the relevant apparatus component or area, for example a reservoir, a pipe, a line, a tube, or the like. In particular, the supply is preferably resistant to elevated and/or decreased temperature and/or pressure. A good temperature and/or pressure resistance is particularly preferred if one or more of the reactions which should take place in the apparatus according to the invention is a gas phase reaction. The supply is furthermore made of a material which is not reactive with any of the components of the feed composition, nor with any further component or components which might be added to the feed composition, as mentioned above in connection with the process according to the invention, preferably made of stainless steel.

The invention also relates to a process according to the invention for preparation of methacrylic acid, wherein said process is performed in an apparatus according to the invention.

The invention also relates to methacrylic acid obtainable by a process according to the invention.

The invention also relates to a process according to the invention for preparation of methyl methacrylate, wherein said process is performed in an apparatus according to the invention.

The invention also relates to methyl methacrylate obtainable by a process according to the invention.

The invention also relates to a process for preparation of a methacrylate ester with formula $[CH_2=C(CH_3)C(=O)O]_n$—R, comprising process steps α1 preparation of methacrylic acid according to a process according to any one of claims 1 to 10 or 19; or α2 preparation of methyl methacrylate according to a process according to any one of claims 2 to 10 or 21; and α3 reaction of the methacrylic acid obtained in step α1 or of the methyl methacrylate obtained in step α2 with an alcohol of formula $R(OH)_m$, whereby n and m represent an integer from 1 to 10, preferably from 1 to 6, more preferably from 1 to 5, more preferably from 1 to 4, more preferably from 1 to 3 and R is selected from the group consisting of linear or branched, saturated or unsaturated, aliphatic or aromatic, ring or straight chain hydrocarbons and linear or branched, saturated or unsaturated, aliphatic or aromatic, ring or straight chain hetero-atom-comprising hydrocarbons, for example alkyls, hydroxyalkyls, aminoalkyls, other nitrogen- and/or oxygen-comprising residues, glycols, diols, triols, bisphenols, fatty acid residues, whereby R preferably represents butyl, in particular n-butyl, isobutyl, hydroxyethyl, preferably 2-hydroxyethyl, and hydroxypropyl, preferably 2-hydroxypropyl or 3-hydroxypropyl, ethyl, 2-ethylhexyl, isodecyl, cyclohexyl, isobornyl, benzyl, 3,3,5-trimethyl cyclohexyl, stearyl, dimethylaminoethyl, dimethylaminopropyl, 2-tert-butyl aminoethyl, ethyl triglycol, tetrahydrofurfuryl, butyl diglycol, methoxypolyethylene glycol-350, methoxypolyethylene glycol 500, methoxypolyethylene glycol 750, methoxypolyethylene glycol 1000, methoxypolyethylene glycol 2000, methoxypolyethylene glycol 5000, allyl, ethylene glycol, diethylene glycol, triethylene glycol, polyethylene glycol 200, polyethylene glycol 400, 1,3-butanediol, 1,4-butanediol, 1,6-hexanediol, glycerol, diurethane, ethoxylated bisphenol A, ethoxylated bisphenol A, for example with 10 ethylene oxide units; trimethylolpropane, an ethoxylated $C_{16}$-$C_{18}$ fatty alcohol, optionally, for example, with 25 ethylene oxide units, 2-trimethylammonium ethyl.

The methacrylate ester derivatives can be prepared in step α3 from methyl methacrylate by methods known to the skilled person, for example by transesterification. Alternatively, these derivatives may be prepared in step α3 by esterification of methacrylic acid according to the invention with the respective alcohol. In a further possible preparation of the hydroxyester derivatives, methacrylic acid according to the invention is reacted in a ring-opening reaction with a corresponding oxygen-comprising ring, for example an epoxide, in particular ethylene oxide or propylene oxide.

The invention also relates to a methacrylate ester with formula $[CH_2=C(CH_3)C(=O)O]_n$—R, wherein n and R are as defined above. Preferred methacrylate esters are alkyl methacrylates, in particular butyl methacrylates, in particular n-butyl methacrylate, isobutyl methacrylate, hydroxyester methacrylate derivatives, for example hydroxyethyl methacrylate, preferably 2-hydroxyethyl methacrylate, and hydroxypropyl methacrylate, preferably 2-hydroxypropyl methacrylate or 3-hydroxypropyl methacrylate, and special methacrylate esters ethyl methacrylate, 2-ethylhexyl methacrylate, isodecyl methacrylate, cyclohexyl methacrylate, isobornyl methacrylate, benzyl methacrylate, 3,3,5-trimethyl cyclohexyl methacrylate, stearyl methacrylate, dimethylaminoethyl methacrylate, dimethylaminopropyl methacrylate, 2-tert-butyl aminoethyl methacrylate, ethyl triglycol methacrylate, tetrahydrofurfuryl methacrylate, butyl diglycol methacrylate, methoxypolyethylene glycol-350 methacrylate, methoxypolyethylene glycol 500 methacrylate, methoxypolyethylene glycol 750 methacrylate, methoxypolyethylene glycol 1000 methacrylate, methoxypolyethylene glycol 2000 methacrylate, methoxypolyethylene glycol 5000 methacrylate, allyl methacrylate, a methacrylic ester of an ethoxylated (optionally, for example, with 25 mol EO) $C_{16}$-$C_{18}$ fatty alcohol, 2-trimethylammonium ethyl methacrylate chloride; ethylene glycol dimethacrylate, diethylene glycol dimethacrylate, triethylene glycol dimethacrylate, polyethylene glycol 200 dimethacrylate, polyethylene glycol 400 dimethacrylate, 1,3-butanediol dimethacrylate, 1,4-butanediol dimethacrylate, 1,6-hexanediol dimethacrylate, glycerol dimethacrylate, diurethane dimethacrylate, ethoxylated bisphenol A dimethacrylate, ethoxylated (optionally, for example, with 10 EO) bisphenol A dimethacrylate; trimethylolpropane trimethacrylate.

The invention further relates to a process for producing a polymer comprising at least one monomer unit selected from methacrylic acid, methyl methacrylate and a methacrylic ester with formula $[CH_2=C(CH_3)C(=O)O]_n$—R, wherein n and R are as defined above, comprising the steps:

A1. preparation of at least one of methacrylic acid, methyl methacrylate and at least one methacrylate ester according to a process according to the invention, A2. polymerisation of
- A2a. at least one of the methacrylic acid, the methyl methacrylate and the at least one methacrylate ester obtained in step A1, and
- A2b. optionally at least one co-monomer which is co-polymerisable with at least one of methacrylic acid, methyl methacrylate and at least one methacrylate ester.

The polymerisation is not particularly limited and can be carried out by any method known to the skilled person and appearing suitable, for example as described in U.S. Pat. No. 5,292,797, U.S. Pat. No. 4,562,234, U.S. Pat. No. 5,773,505, U.S. Pat. No. 5,612,417, U.S. Pat. No. 4,952,455, U.S. Pat. No. 4,948,668, U.S. Pat. No. 4,239,671. Preferred polymerisation methods are radical polymerisation, initiated by initiators which decompose into radicals under the polymerisation conditions, whereby the polymerisation is preferably a solution or an emulsion polymerisation, preferably an aqueous solution polymerisation.

Examples of co-monomers which can be co-polymerised with methyl methacrylate are acrylamides and methacrylamides, acrylic acid esters and other methacrylic acid esters, such as methyl acrylate, ethyl acrylate, propyl acrylate or butyl acrylate, ethyl methacrylate, propyl methacrylate or butyl methacrylate, as well as acetates such as vinyl acetate, styrene, butadiene and acrylonitrile. The at least one co-monomer is most preferably at least one co-monomer selected from the group consisting of: styrene, butadiene, acrylonitrile, butyl acrylate, vinyl acetate, methyl acrylate.

The polymerisation can also take place in the presence of one or more crosslinkers. Preferred cross-linkers according to the invention are compounds which have at least two ethylenically unsaturated groups in one molecule, compounds which have at least two functional groups which can react with functional groups of the monomers in a condensation reaction, in an addition reaction or a ring-opening reaction, compounds which have at least one ethylenically unsaturated group and at least one functional group which can react with functional groups of the monomers in a condensation reaction, an addition reaction or a ring-opening reaction, or polyvalent metal cations.

The invention also relates to a polymer obtainable according to a process according to the invention or comprising at least one monomer unit selected from a methacrylic acid monomer according to the invention or obtainable by a process according to the invention, a methyl methacrylate monomer according to the invention or obtainable by a process according to the invention and a methacrylate ester according to the invention or obtainable by a process according to the invention, as well as optionally other components such as a co-monomer and optionally a crosslinker.

The invention also relates to a process for producing a composition comprising at least a first component selected from at least one of methacrylic acid according to the invention, methyl methacrylate according to the invention, a methacrylate ester according to the invention, and a polymer comprising at least one monomer unit selected from methacrylic acid, methyl methacrylate and a methacrylate ester, comprising the steps:

B1. providing at least one first component selected from methacrylic acid according to the invention, methyl methacrylate according to the invention, a methacrylate ester according to the invention, and a polymer according to the invention comprising at least one monomer unit selected from methacrylic acid, methyl methacrylate and a methacrylate ester, B2. combining the at least one first component provided in B1 with at least one further component.

The at least one further component is preferably at least one component selected from natural or synthetic organic or inorganic polymers, for example selected from a substituted or unsubstituted polystyrene, poly-n-butyl acrylate, a polyacrylonitrile, a polysaccharide, a silica, and a nanomaterial.

The invention also relates to a composition comprising at least one first component selected from methacrylic acid according to the invention, methyl methacrylate according to the invention, a methacrylate ester according to the invention, and a polymer according to the invention comprising at least one monomer unit selected from methacrylic acid, methyl methacrylate and a methacrylate ester and at least one further component, or obtainable according to a process according to the invention.

In the composition according to the invention, the at least one further component is preferably at least one component as described above in connection with the process for producing a composition.

The invention also relates to chemical products such as a shaped article, a moulding material, a film, a sheet, a granulate, a composite, a foam, a fibre, a lubricant, an adhesive, a thickening agent, a suspending agent, a flocculant, a resin, a plastic, a coating, a contact lens, a construction material, an absorbent material, a pharmaceutical, a material for controlled release of active substances, a foam, a fibre, a lubricant, a powder or a particle comprising at least one of methacrylic acid according to the invention, methyl methacrylate according to the invention, methacrylate ester according to the invention, a polymer or co-polymer according to the invention which comprises methacrylic acid, methyl methacrylate, and/or a methacrylate ester, and a composition according to the invention.

The invention also relates to a use of at least one of methacrylic acid according to the invention, methyl methacrylate according to the invention, methacrylate ester according to the invention, a polymer or co-polymer according to the invention which comprises methacrylic acid, methyl methacrylate, and/or a methacrylate ester, and a composition according to the invention, in chemical products such as shaped articles, moulding materials, films, sheets, granulates, composites, adhesives, thickening agents, suspending agents, flocculants, resins, plastics, coatings, contact lenses, construction materials, absorbent materials, pharmaceuticals, materials for controlled release of active substances, foams, fibres, lubricants, powders, particles.

The invention is now illustrated with non-limiting FIGURE and examples.

DESCRIPTION OF THE FIGURES

FIG. 1 shows schematically a preferred embodiment of the apparatus 1 according to the invention.

A $C_4$ fraction from a cracker (not shown) is treated in treatment unit 12 to obtain a desired composition and is supplied via supply 2 to first catalytic reaction zone 4. Methanol is supplied via supply 3 to first catalytic reaction zone 4. In catalytic reaction zone 4, methanol and isobutylene are reacted to form MTBE. The effluent of first catalytic reaction zone 4 is conducted to first separating unit 5, where MTBE and methanol phases are separated. The methanol phase is conducted to methanol supply 11. The MTBE phase is conducted to mixing unit 6 and optionally mixed with MTBE from another source which is conducted to mixing unit 6 by means of supply 16. The MTBE phase exiting mixing unit 6 is conducted to second catalytic reaction zone 7, where it is split to form principally isobutylene and methanol. The effluent of second catalytic reaction zone 7 is conducted to second separation unit 8, where a first isobutylene phase and a methanol phase are separated. The methanol phase is conducted to methanol supply 17 and the first isobutylene phase is conducted to purification unit 18, where impurities, as well as a further methanol phase, can be separated. The further methanol phase is conducted to methanol supply 17. The purified first isobutylene phase is then conducted to the third catalytic reaction zone 9, comprising oxidation areas 14a and 14b, together with intermediate optional quench unit 22. Each oxidation area 14a, 14b, which may be comprised in one or more oxidation units 33 (not shown for the sake of clarity), is supplied with air, steam and diluent by means of air supply 19, steam supply 20 and diluent supply 21 respectively. Diluent supply 21 is optionally supplied with diluent from a recycle flow 15 from quench unit 23 and/or purification unit 25, optionally via a combustion unit 34 (recycle flow 15 and combustion unit 34 are not shown for the sake of clarity). In first oxidation area 14a, methacrolein is formed as main product from oxidation of isobutylene and in second oxidation area 14b, methacrylic acid is formed as main product of oxidation of methacrolein. The methacrylic acid-rich effluent exiting the third catalytic reaction zone 9 is conducted to quench unit 23, where methacrylic acid is transferred into aqueous form. The methacrylic acid phase is then conducted to third purification unit 25 for purification of methacrylic acid. In one or both of quench unit 23 and purification unit 25, methacrolein can be separated.

Separated methacrolein is conducted back by means of methacrolein recycle conduit 24 to the second oxidation area 14b for further oxidation reaction. The methacrylic acid phase exiting third purification unit 25 can be collected or can be conducted to fourth catalytic reaction zone 10. The methanol phase separated in first separating unit 5, optionally purified in purification unit 31, is also supplied to fourth catalytic reaction zone 10 by means of methanol supply 11. The methacrylic acid and the methanol react in fourth catalytic reaction zone 10 to form a methyl methacrylate phase comprising methyl methacrylate as main product. The methyl methacrylate phase can be purified in purification unit 30. Unreacted methanol and methacrylic acid can also be separated in purification unit 30. Methanol can be recycled to first catalytic reaction zone 4, to fourth catalytic reaction zone 10, or to third catalytic reaction zone 9, optionally with an intermediate purification. Methacrylic acid can be recycled to fourth catalytic reaction zone 10, optionally with an intermediate purification, for example in third purification unit 25. Alternatively, methanol and/or methacrylic acid in the effluent of fourth catalytic reaction zone 10 can be conducted away.

The third catalytic reaction zone illustrated in FIG. 1 as a two-stage oxidation zone can also be considered as a one-stage oxidation zone. In this embodiment, the purified isobutylene phase is conducted to third catalytic reaction zone 9, comprising an oxidation area 14. In oxidation area 14, methacrolein is formed and converted continuously to methacrylic acid.

EXAMPLES

I) Preparation of MTBE

Process Steps a), b) and c)

The procedure of U.S. Pat. No. 6,657,090 B2 was followed, starting from feedstocks according to tables 1 to 3 of that patent. The yield of MTBE given is calculated based on the amount of MTBE in the product stream, before any purification step or steps.

TABLE 1

| Feed | Moles | Molar ratio (based on IBEN) | Yield (based on IBEN) |
|---|---|---|---|
| $C_4$* | 100 | — | — |
| - of which IBEN | 47 | 1 | — |
| MeOH | 49.6 | 1.3 | — |
| Product MTBE | 45.64 | — | 98.3% |

*$C_4$ = IBEN, n-butene, butanes, as well as about 1% $C_3$ and smaller hydrocarbons.

The purity of the MTBE is approximately 84% due to azeotrope formation with 14.5% methanol.

II) Separation of Methanol from MTBE-Phase

Process Step d)

The azeotrope was separated into methanol and MTBE by processes known to the skilled person from J. G. Stichlmair, J. R. Fair, "*Distillation: Principles and Practice*", Wiley-VCH, 2001, p. 238.

TABLE 2

| Feed | Moles | Molar ratio (based on IBEN) | Yield (based on IBEN) |
|---|---|---|---|
| $C_4$* | 100 | — | — |
| - of which IBEN | 92 | 1 | — |
| MeOH | 120.1 | 1.3 | — |
| Product MTBE | 91.01 | — | 98.5% |

*C4 = IBEN, n-butene, butanes, as well as about 1% $C_3$ and smaller hydrocarbons.

III) Splitting of MTBE

Process Steps e), f), g)

The procedure of Example 1 of DE 102 38 370 A1 was followed, starting from a composition obtained in Example II above, consisting of 91.01% MTBE, <2% methanol, <0.1% TBA and <0.1% $H_2O$. A splitting phase was obtained with composition 97.5 wt. % IBEN, 3.05 wt. % MeOH, 0.05 wt. % DME, 0.04 wt. % $H_2O$.

IV) Two-Stage Oxidation of Isobutylene to Methacrylic Acid

Process Step h)

The composition obtained in Example III was oxidised to methacrolein according to the process and under the conditions of Example 15 of EP 0 807 465 A1. The following feed composition has been used (Table 3):

TABLE 3

| | Mol | Mol % |
|---|---|---|
| IBEN | 1 | 6 |
| $O_2$ | 2 | 13 |
| $N_2$ | 8 | 51 |
| $H_2O$ | 1.8 | 11 |
| $N_2/CO_2$ | 3 | 19 |

To the first oxidation phase resulting from this first oxidation were then added $O_2$, $H_2O$ and diluent gases in molar amounts according to Table 4, based on the number of moles IBEN in the feed composition subjected to the first oxidation reactor.

This feed was then subjected to a second oxidation reactor. In this second reactor, methacrolein was oxidised to methacrylic acid according to the process and under the conditions of Example 1 of EP 1 325 780 A1.

TABLE 4

| | Mol | Mol % |
|---|---|---|
| methacrolein | 0.8 | 4 |
| $O_2$ | 1 | 5 |
| $N_2$ | 12 | 59 |
| $H_2O$ | 3.5 | 17 |
| $N_2/CO_2$ | 3 | 15 |

A yield of 60% methacrylic acid was obtained, based on the number of moles of IBEN introduced into the first oxidation reactor.

V) Preparation of Methyl Methacrylate

Process Step j)

One mole of the methacrylic acid obtained in Example IV) was converted to methyl methacrylate by reaction with 1.2 moles methanol, in a liquid phase reaction in a fixed bed reactor packed with an acidic ion exchange resin as described in EP 1 254 887 A1, with the difference that Amberlyst® (Rohm & Haas Corp.) is used as acidic ion exchange resin. The methanol used was the methanol separated according to Example II above, supplemented by solvent grade methanol to make up the desired amount. The conversion of methacrylic acid to methyl methacrylate was 45%, based on methacrylic acid.

VI) Preparation of n-Butyl Methacrylate n-Butyl methacrylate was prepared according to the process of Example 2 of DE 103 01 007 A1 by transesterification of the methyl methacrylate obtained in Example V above.

| REFERENCE NUMBERS | |
|---|---|
| 1 | apparatus |
| 2 | supply for $C_4$ feed compound |
| 3 | supply for methanol |
| 4 | first catalytic reaction zone |
| 5 | first separation unit |
| 6 | mixing unit |
| 7 | second catalytic reaction zone |
| 8 | second separation unit |
| 9 | third catalytic reaction zone |
| 10 | fourth catalytic reaction zone |
| 11 | methanol supply |
| 12 | treatment unit |
| 13 | methanol outlet |
| 14 | oxidation area |
| 14a | first oxidation area |
| 14b | second oxidation area |
| 15 | diluent recycle flow |
| 16 | MTBE supply |
| 17 | methanol supply |
| 18 | second purification unit |
| 19 | air supply |
| 20 | water supply |
| 21 | diluent supply |
| 22 | intermediate quench unit |
| 23 | quench unit |

-continued

| REFERENCE NUMBERS | |
|---|---|
| 24 | methacrolein recycle conduit |
| 25 | second purification unit |
| 26 | methacrylic acid outlet |
| 27 | methacrylic acid recycle |
| 28 | methanol recycle |
| 29 | methyl methacrylate outlet |
| 30 | third purification unit |
| 31 | methanol purification unit |
| 32 | methanol purification unit |
| 33 | oxidation unit |
| 34 | combustion unit |

The invention claimed is:

1. A process for production of methacrylic acid, comprising
    a) providing a feed composition comprising at least one $C_4$ feed compound selected from the group consisting of isobutylene and tertiary butanol;
    b) providing methanol;
    c) subjecting the at least one $C_4$ feed compound and the methanol to a first catalytic reaction zone to obtain a reaction phase comprising methyl tertiary butyl ether
    d) separating at least a first part of methanol from the reaction phase to obtain a first methanol phase and a reaction phase depleted in methanol;
    e) subjecting at least one of the reaction phase and the reaction phase depleted in methanol to a second catalytic reaction zone to obtain a splitting phase comprising isobutylene and methanol;
    f) optionally separating at least a first part of isobutylene from the splitting phase to obtain a first isobutylene phase and a splitting phase depleted in isobutylene;
    g) optionally subjecting at least one of the splitting phase and the first isobutylene phase to a first purification zone;
    h) subjecting at least one of the splitting phase, optionally subjected to the first purification zone in g), and the first isobutylene phase, optionally subjected to the first purification zone in g), to a third catalytic reaction zone to obtain an oxidation phase comprising at least one $C_4$ oxidation product selected from the group consisting of methacrolein and methacrylic acid; and
    i) optionally subjecting the oxidation phase to a second purification zone.

2. A process for production of methyl methacrylate, comprising
    a) providing a feed composition comprising at least one $C_4$ feed compound selected from isobutylene and tertiary butanol;
    b) providing methanol;
    c) subjecting the at least one $C_4$ feed compound and the methanol to a first catalytic reaction zone to obtain a reaction phase comprising methyl tertiary butyl ether
    d) separating at least a first part of methanol from the reaction phase to obtain a first methanol phase and a reaction phase depleted in methanol;
    e) subjecting at least one of the reaction phase and the reaction phase depleted in methanol to a second catalytic reaction zone to obtain a splitting phase comprising isobutylene and methanol;
    f) optionally separating at least a first part of isobutylene from the splitting phase to obtain a first isobutylene phase and a splitting phase depleted in isobutylene;
    g) optionally subjecting at least one of the splitting phase and the first isobutylene phase to a first purification zone;
    h) subjecting at least one of the splitting phase, optionally subjected to the first purification zone in g), and the first isobutylene phase, optionally subjected to the first purification zone in g), to a third catalytic reaction zone to obtain an oxidation phase comprising at least one $C_4$ oxidation product selected from the group consisting of methacrolein and methacrylic acid;
    i) optionally subjecting the oxidation phase to a second purification zone;
    j) subjecting the oxidation phase, optionally subjected to the second purification zone in i), to a fourth catalytic reaction zone to obtain an esterification phase comprising methyl methacrylate; and
    k) optionally subjecting the esterification phase to a third purification zone.

3. The process according to claim 1, wherein in b) the methanol is provided in a molar ratio of methanol to $C_4$ feed compound of 10 to 1, based on the number of moles of $C_4$ feed compound.

4. The process according to claim 2, wherein at least a part of the first methanol phase is provided to the fourth catalytic reaction zone.

5. The process according to claim 1, wherein in f) a second methanol phase is separated.

6. The process according to claim 5, wherein at least a part of the second methanol phase is provided to at least one of the first catalytic reaction zone and the fourth catalytic reaction zone.

7. The process according to claim 1, wherein in h) at least a part of the first isobutylene phase is subjected to oxidation.

8. The process according to claim 7, wherein the oxidation takes place in at least two separate oxidation stages.

9. The process according to claim 8, wherein a first oxidation stage produces methacrolein and a further oxidation stage produces methacrylic acid.

10. The process according to claim 1, wherein at least h) occurs at least partially in the gas phase.

11. A process for preparation of a methacrylate ester with formula $[CH_2=C(CH_3)C(=O)O]_n$—R, comprising
    α2 preparing methyl methacrylate according to claim 2; and
    α3 reacting the methyl methacrylate obtained in α2 with an alcohol of formula $R(OH)_m$,
    wherein n and m represent an integer from 1 to 10, and
    R is selected from the group consisting of linear or branched, saturated or unsaturated, aliphatic or aromatic, ring or straight chain hydrocarbons and linear or branched, saturated or unsaturated, aliphatic or aromatic, and ring or straight chain heteroatom-comprising hydrocarbons.

12. A process for producing a polymer comprising at least one monomer unit selected from the group consisting of methacrylic acid, methyl methacrylate and a methacrylic ester with formula $[CH_2=C(CH_3)C(=O)O]_n$—R, wherein
    n represents an integer from 1 to 10, and
    R is selected from the group consisting of linear or branched, saturated or unsaturated, aliphatic or aromatic, ring or straight chain hydrocarbons and linear or branched, saturated or unsaturated, aliphatic or aromatic, and ring or straight chain hetero-atom-comprising hydrocarbons,
    comprising:
    A1. preparing methyl methacrylate according to claim 2,
    A2. polymerisation of
    A2a. the methyl methacrylate obtained in A1, and A2b. optionally at least one co-monomer which is co-polymerisable with at least one of methacrylic acid, methyl methacrylate and methacrylate ester.

13. The process according to claim 12, wherein the at least one co-monomer is at least one co-monomer selected from the group consisting of: styrene, butadiene, acrylonitrile, butyl acrylate, vinyl acetate, and methyl acrylate.

14. A process for preparation of a methacrylate ester with formula $[CH_2=C(CH_3)C(=O)O]_n-R$, comprising α1 preparing methacrylic acid according to a process according to claim 1; and α3 reacting the methacrylic acid obtained in α1 with an alcohol of formula $R(OH)_m$, wherein n and m represent an integer from 1 to 10, and R is selected from the group consisting of linear or branched, saturated or unsaturated, aliphatic or aromatic, ring or straight chain hydrocarbons and linear or branched, saturated or unsaturated, aliphatic or aromatic, and ring or straight chain heteroatom-comprising hydrocarbons.

15. The process according to claim 1, wherein the feed composition comprises tertiary butanol.

16. The process according to claim 1, further comprising: reacting the methanol separated from the reaction phase in (d) with methacrylic acid formed in the third catalytic reaction zone to form methyl methacrylate.

17. The process according to claim 2, wherein the feed composition comprises tertiary butanol.

18. The process according to claim 2, wherein the oxidation phase is combined with the methanol separated from the reaction phase in (d) to form the methyl methacrylate in the fourth catalytic reaction zone.

* * * * *

UNITED STATES PATENT AND TRADEMARK OFFICE
CERTIFICATE OF CORRECTION

PATENT NO. : 8,350,081 B2  
APPLICATION NO. : 12/597540  
DATED : January 8, 2013  
INVENTOR(S) : Torsten Balduf Page 1 of 1

It is certified that error appears in the above-identified patent and that said Letters Patent is hereby corrected as shown below:

On the title page, Item (54), and in the specification, column 1, the title is incorrect, it should read:

--PROCESS FOR PREPARATION OF METHYL METHACRYLATE USING RECYCLED METHANOL--

Signed and Sealed this
Twenty-eighth Day of May, 2013

Teresa Stanek Rea
*Acting Director of the United States Patent and Trademark Office*